United States Patent [19]

Kimura et al.

[11] Patent Number: 4,822,402
[45] Date of Patent: Apr. 18, 1989

[54] THIOPHENESULFONAMIDE COMPOUNDS, AND HERBICIDAL COMPOSITIONS CONTAINING THEM

[75] Inventors: Fumio Kimura, Otsu; Takahiro Haga, Kusatsu; Kazuyuki Maeda, Hikone; Koji Hayashi; Masahiko Ikeguchi, both of Moriyama; Tsunezo Yoshida, Kusatsu, all of Japan

[73] Assignee: Ishihara Sangyo Kaisha Ltd., Osaka, Japan

[21] Appl. No.: 865,467

[22] Filed: May 21, 1986

[30] Foreign Application Priority Data

Jun. 7, 1985 [JP] Japan .................. 60-123901
Sep. 20, 1985 [JP] Japan .................. 60-207830

[51] Int. Cl.⁴ .................. C07D 409/12; A01N 43/54
[52] U.S. Cl. .................. 71/90; 544/320; 544/331
[58] Field of Search .................. 71/90; 544/320, 331

[56] References Cited

U.S. PATENT DOCUMENTS

| | | | |
|---|---|---|---|
| 4,120,691 | 10/1978 | Levitt | 71/93 |
| 4,169,719 | 10/1979 | Levitt | 71/92 |
| 4,398,939 | 8/1983 | Levitt | 71/90 |
| 4,521,597 | 6/1985 | Kristinsson et al. | 544/321 |
| 4,620,868 | 11/1986 | Kimura et al. | 71/90 |
| 4,743,290 | 5/1988 | Christensen et al. | 544/320 |

Primary Examiner—John M. Ford
Attorney, Agent, or Firm—Oblon, Fisher, Spivak, McClelland & Maier

[57] ABSTRACT

A thiophenesulfonamide compound having the formula:

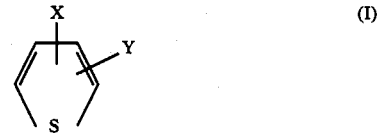

wherein X is a halogenoalkoxyalkyl group, and Y is

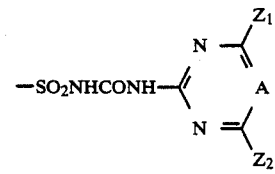

wherein A is $=N-$ or $=CH-$, and each of $Z_1$ and $Z_2$ is a methyl group or a methoxy group, and its salt.

13 Claims, No Drawings

THIOPHENESULFONAMIDE COMPOUNDS, AND HERBICIDAL COMPOSITIONS CONTAINING THEM

BACKGROUND OF THE INVENTION

1. Field of ohe Invention

The present invention relates to novel thiophenesulfonamide compounds and salts thereof, herbicidal compositions containing them as active ingredients, and a process for their production.

2. Description of the Prior Art

Sulfonamide compounds having a thiophene ring are disclosed in U.S. Pat. Nos. 4,120,691, 4,169,719, 4,398,939 and 4,521,597. However, in these compounds, the thiophene ring is either unsubstituted or substituted by an alkyl group, an alkoxy group or a trifluoromethyl group. Whereas, the thiophenesulfonamide compounds of the present invention are characterized in that the thiophene ring has a halogenoalkoxyalkyl group, and thus they are substantially different from the above-mentioned sulfonamide compounds in their chemical structure.

SUMMARY OF THE INVENTION

The present invention provides a thiophenesulfonamide compound having the formula:

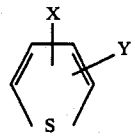
(I)

wherein X is a halogenoalkoxyalkyl group, and Y is

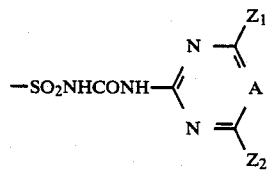

wherein A is =N— or =CH—, and each of $Z_1$ and $Z_2$ is a methyl group or a methoxy group, and its salt.

The present invention also provides a process for producing the compound of the formula I, which comprises reacting a thiophene compound having the formula:

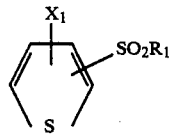
(II)

wherein $X_1$ is a halogenoalkoxyalkyl group or a monobromoalkyl group, and $R_1$ is an amino group, an isocyanato group or

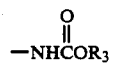

wherein $R_3$ is an alkyl group, an alkenyl group or a phenyl group, with a heterocyclic compound having the formula:

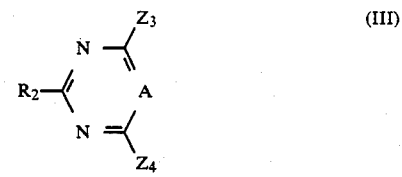
(III)

wherein A is as defined above, each of $Z_3$ and $Z_4$ is a methyl group, a methoxy group or a halogen atom, and $R_2$ is

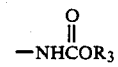

wherein $R_3$ is as defined above, an amino group or an isocyanato group, provided that when $R_1$ is an amino group, $R_2$ is

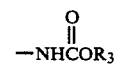

or an isocyanato group, and when $R_2$ is an amino group, $R_1$ is an isocyanato group or

followed by halogenoalkoxylation when $X_1$ is a monobromoalkyl group, or by methoxylation when $Z_3$ and/or $Z_4$ is a halogen atom.

Further, the present invention provides a herbicidal composition comprising a herbicidally effective amount of the compound of the formula I or its salt, and an agricultural adjuvant.

Furthermore, the present invention provides a method for killing weeds, which comprises applying a herbicidally effective amount of the compound of the formula I or its salt to the locus to be protected.

DETAILED DESCRIPTION OF THE PREFERRED EMBODIMENTS

In the formula I, the halogenoalkoxyalkyl as X contains a halogenoalkoxy moiety having from 1 to 6 halogen atoms, preferably from 1 to 4 halogen atoms. The halogen includes chlorine, bromine and fluorine, and fluorine is particularly preferred. When a plurality of halogen atoms are present, they may be the same or different one another. The alkoxy moiety usually has from 1 to 6 carbon atoms, preferably from 1 to 3 carbon atoms. For instance, the alkoxy moiety includes a methoxy group, an ethoxy group, a propoxy group and a butoxy group, and particularly preferred is an ethoxy group. The alkyl group includes a methyl group and an ethyl group, and preferred is a methyl group. Further, when A is =CH—, each of $Z_1$ and $Z_2$ is preferably a methoxy group.

The thiophenesulfonamide compounds of the formula I may form salts with an alkali metal such as sodium or potassium, with an alkaline earth metal such as magnesium or calcium, and with an amine such as dimethylamine or triethylamine.

As mentioned above, the compounds of the formula I of the present invention can be prepared by reacting the thiophene compound of the formula II with a heterocyclic compound of the formual III, followed by halogenoalkoxylation when $X_1$ is a monobromoalkyl group, or by methoxylation when $Z_3$ and/or $Z_4$ is a halogen atom.

Specifically, the compounds of the present invention may be prepared by the following processes:

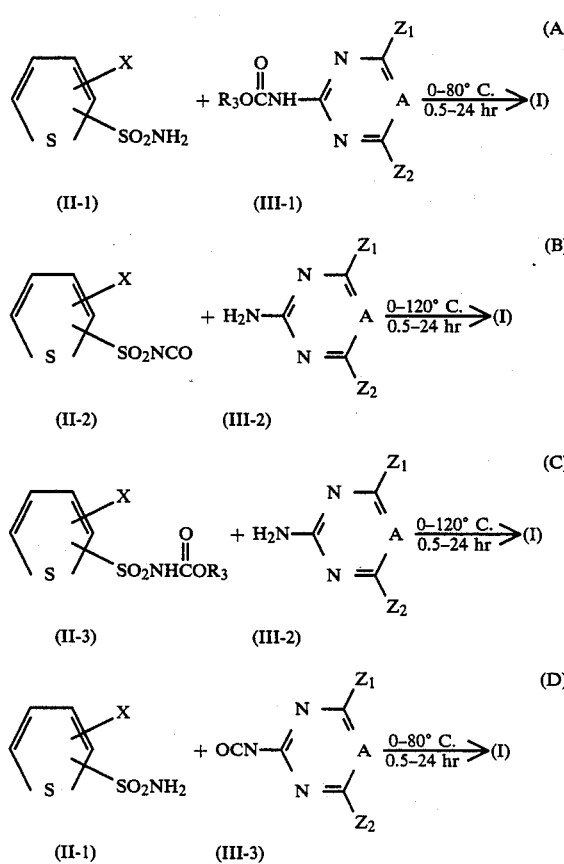

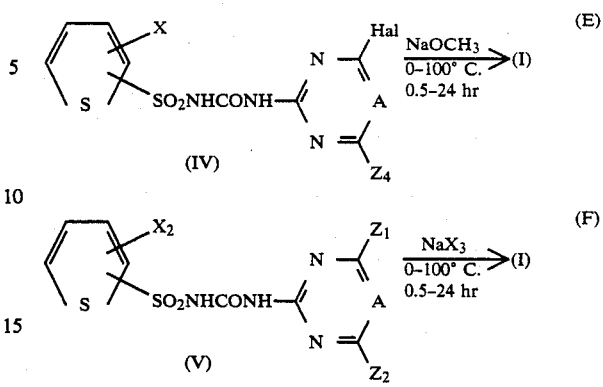

In the above formulas, A, $R_3$, X, $Z_1$, $Z_2$ and $Z_4$ are as defined above, Hal is a halogen atom, $X_2$ is a monobromo alkyl group, and $X_3$ is a halogenoalkoxy group. The starting materials of the formulas IV and V in the above processes E and F can be prepared in accordance with the preceeding processes A to D.

The above reactions may be conducted in the presence of a solvent, as the case requires.

The solvent includes an aromatic hydrocarbon such as benzene, toluene, xylene or chlorobenzene; a cyclic or acyclic aliphatic hydrocarbon such as chloroform, carbon tetrachloride, methylene chloride, dichloroethane, trichloroethane, hexane or cyclohexane; an ether such as diethyl ether, dioxane or tetrahydrofuran; a ketone such as acetone, methyl ethyl ketone or methyl isobutyl ketone; a nitrile such as acetonitrile, propionitrile or acrylonitrile; and an aprotic polar solvent such as dimethyl sulfoxide or sulfolane.

In the reaction of the above process A, 1,8-diazabicyclo[5.4.0]-7-undecene may be added, as the case requires, to facilitate the reaction. Likewise, in the reactions of the above processes B and D, 1,4-diazabicyclo[2.2.2]octane may be added, as the case requires, as a solvent to facilitate the reaction.

The starting materials of the formulas II-1 to II-3 in the above processes A to D may be prepared, for instance, by the following methods.

(1) From 3-methylthiophene

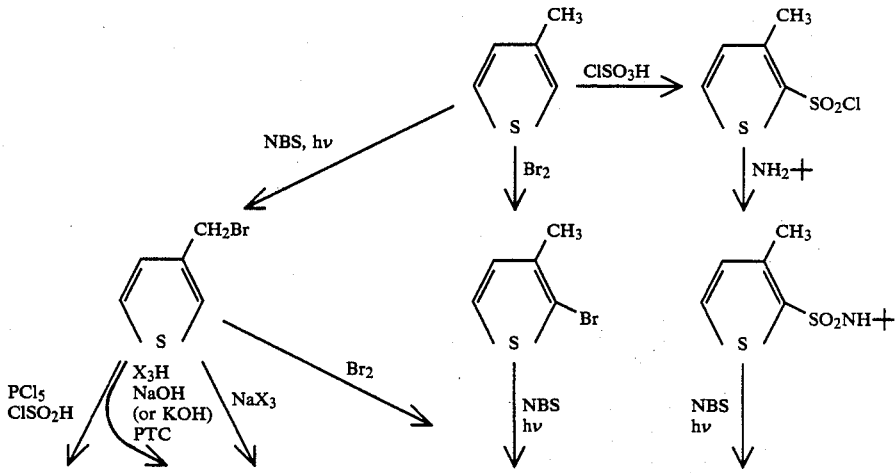

-continued
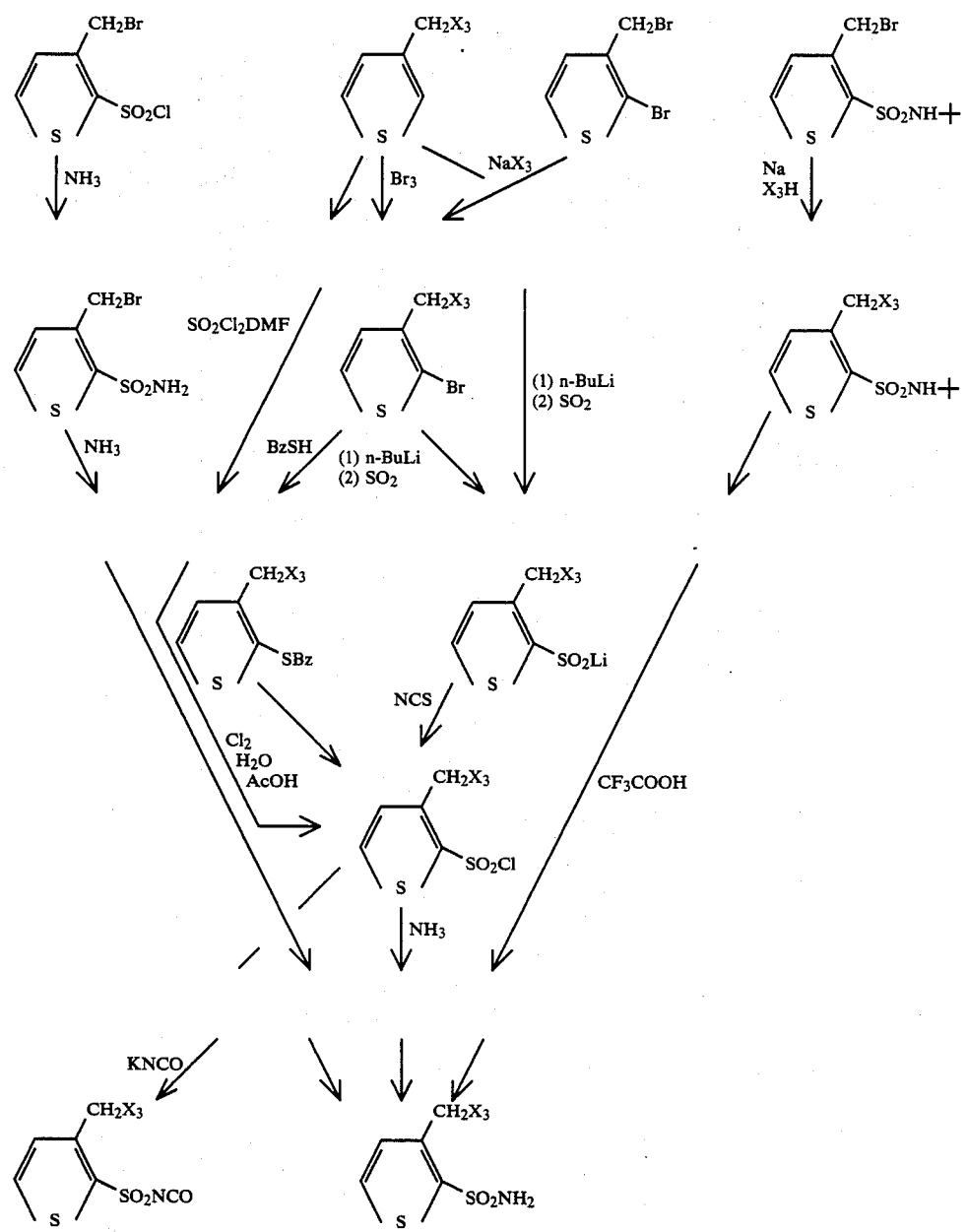
(2) From thiophene

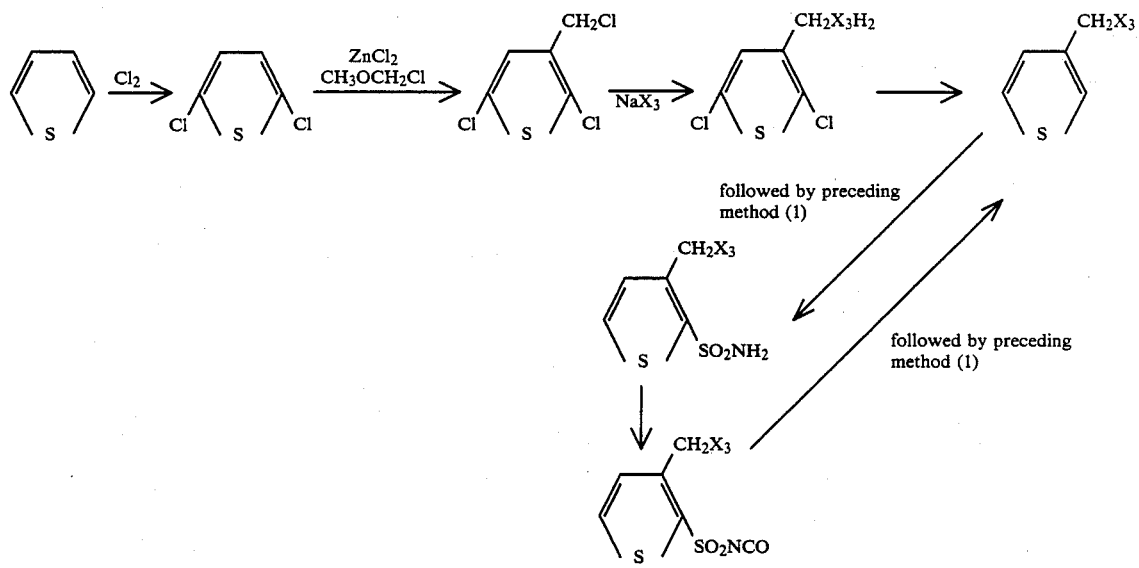
(3) From 3-bromothiophene
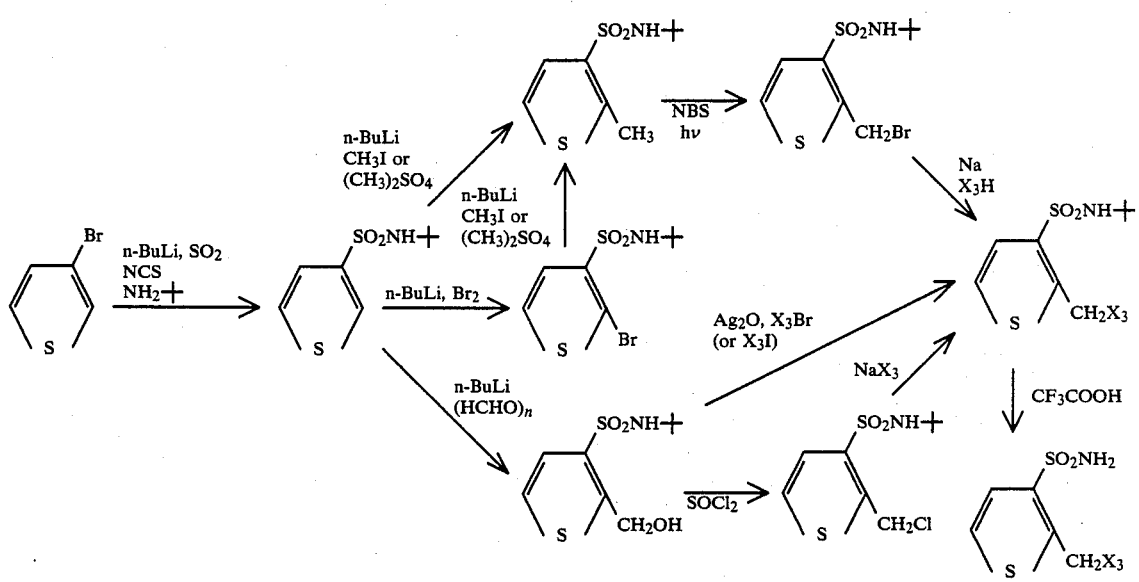
(4) From dibromothiophene, etc.
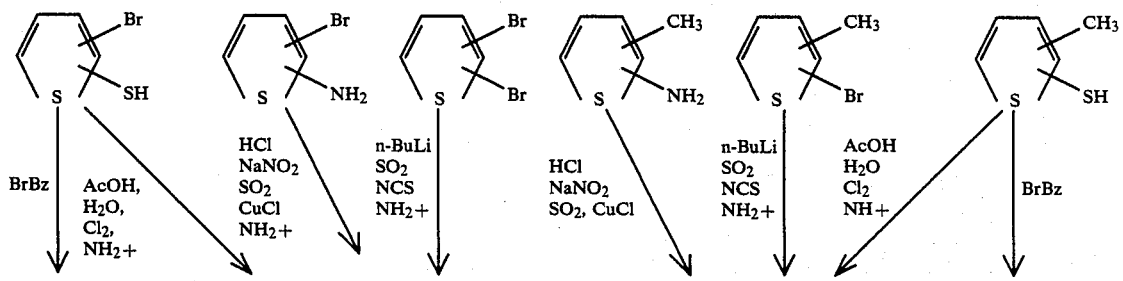

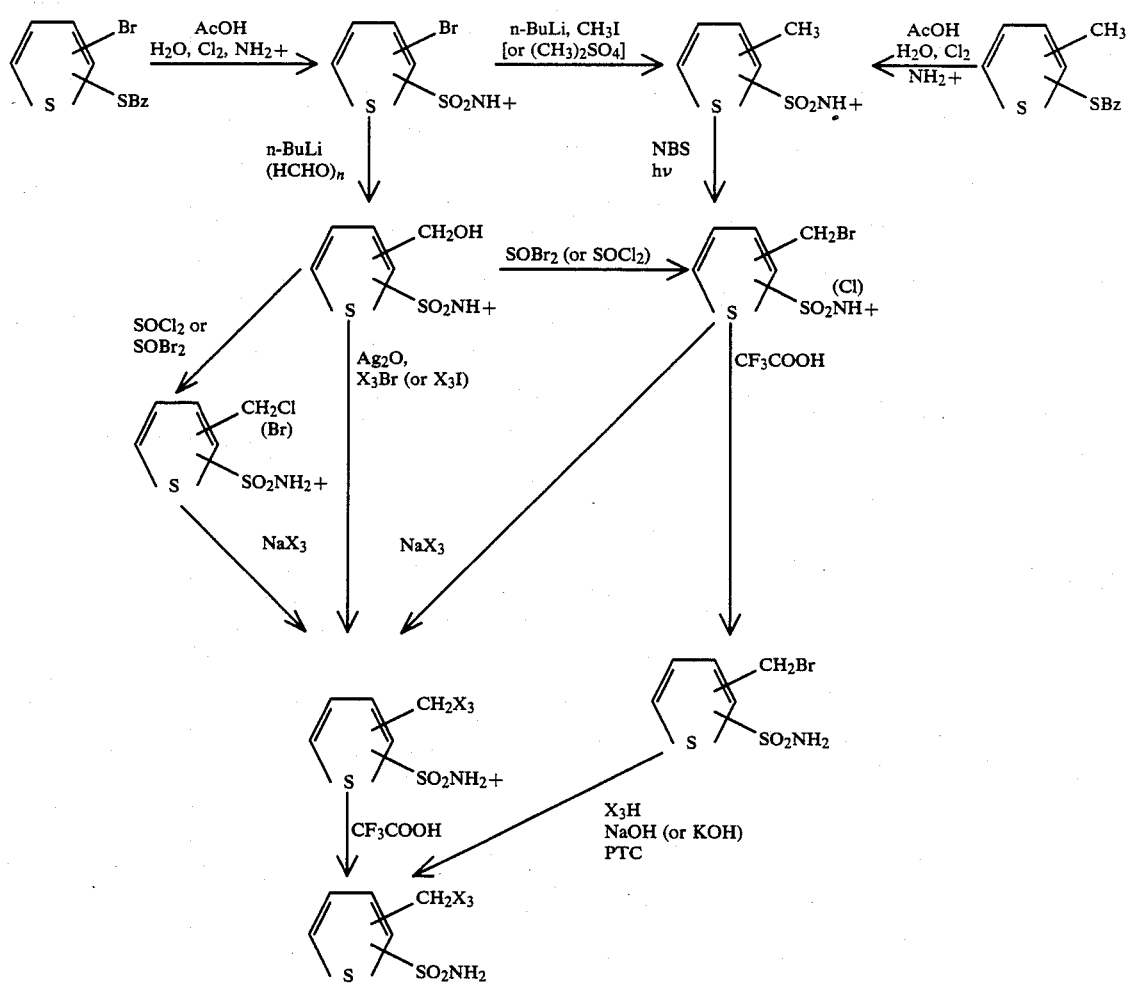
(5)
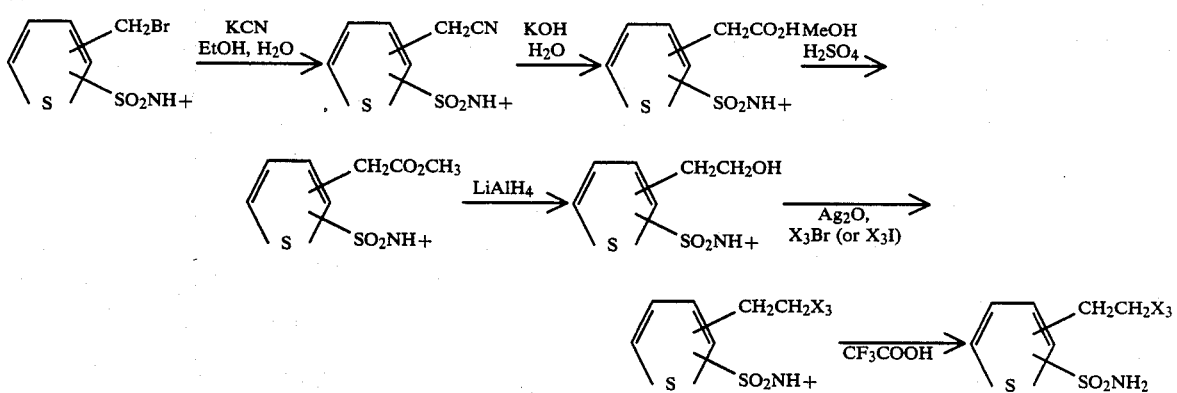
(6)
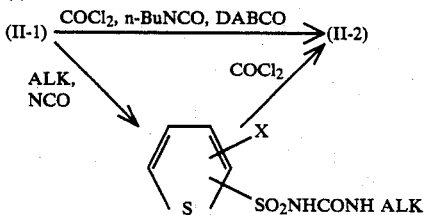
(7)

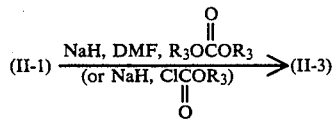

The abbreviations in the above formulas are as follows:

NBS: N—bromosuccinimide
NCS: N—chlorosuccinimide
AcOH: Acetic acid
n-BuLi: n-Butyllithium
DMF: Dimethylformamide
Bz: Benzyl group
$NH_2$ : tert-Butylamine
EtOH: Ethanol
MeOH: Methanol
DABCO: 1,4-Diazabicyclo[2.2.2]octane
Alk: Alkyl group
$(HCHO)_n$: Paraformaldehyde
PTC: Phase transfer catalyst The reaction conditions for the respective reactions for the preparation of the starting materials, such as the reaction temperatures, the reaction times, the solvents or alkaline substances employed as the case requires, etc., may be suitably selected from the reaction conditions for the same types of common reactions.

Now, Synthesis Examples for the preparation of the compounds of the present invention will be described.

SYNTHESIS EXAMPLE 1

Preparation of N-[(4,6-dimethoxypyrimidin-2-yl)aminocarbonyl]-3-(2,2,2-trifluoroethoxymethyl)-2-thiophenesulfonamide (Compound No. 1)

Synthesis of intermediate

[A-1] 9.5 g of 3-methylthiophene was dropwise added to 14 ml of chlorosulfonic acid at a temperature of −50° C. or lower. After the dropwise addition, the mixture was stirred at a temperature of −40° C. or lower for 1.5 hours. Then, the temperature was gradually raised to −10° C., and the stirring was continued at −10° C. for further one hour. The solution thus obtained was poured into ice water in small portions, and then extracted with methylene chloride. The extract layer was washed with water, dried over anhydrous sodium sulfate, and then filtered. To the filtrate, 20.5 ml of tert-butylamine was added, and the mixture was reacted at a refluxing temperature for 17.5 hours.

After the completion of the reaction, the reaction product was cooled and then filtered. The solid substance thereby obtained was washed with ethyl acetate, and the washing solution and the filtrate were put together, then washed with dilute hydrochloric acid and dried over anhydrous sodium sulfate. Then, the solvent was distilled off under reduced pressure, and the residue was purified by silica gel column chromatography (developer: toluene/methylene chloride=1/1) to obtain 4.54 g of N-tert-butyl-3-methyl-2-thiophenesulfonamide having a melting point of from 122° to 125° C.

[A-2] 4.54 g of the sulfonamide obtained in the preceding step [A-1], 50 ml of carbon tetrachloride and 3.82 g of N-bromosuccinimide were mixed and reacted under irradiation at a refluxing temperature for 15.5 hours.

After the completion of the reaction, the reaction product was cooled and then filtered. The solid substance thus obtained was washed with carbon tetrachloride, and all of the filtrates were put together, and the solvent was distilled off under reduced pressure. The residue was purified by silica gel column chromatography (developer: toluene/methylene chloride=1/1) to obtain 5.2 g of 3-bromomethyl-N-tert-butyl-2-thiophenesulfonamide having a melting point of from 88° to 94° C.

[A-3] 0.42 g of sodium was added to 15 ml of 2,2,2-trifluoroethanol, and stirred at room temperature until sodium was completely consumed. A solution obtained by dissolving 2.8 g of the sulfonamide obtained in the preceding step [A-2] in 10 ml of dried methylene chloride, was added thereto, and the mixture was reacted at a refluxing temperature for 15 hours.

After the completion of the reaction, the reaction product was cooled, and after the addition of water, adjusted to a pH of 3 or lower with dilute hydrochloric acid, and then extracted with methylene chloride. The extract layer was dried over anhydrous sodium sulfate, and the solvent was distilled off. The residue was purified by silica gel column chromatography (developer: methylene chloride/n-hexane=8/1) to obtain 2.45 g of N-tert-butyl-3-(2,2,2-trifluoroethoxymethyl)-2-thiophenesulfonamide as an oily substance.

[A-4] 2.45 g of the sulfonamide obtained in the preceding step [A-3] and 12 ml of trifluoroacetic acid were mixed, and reacted at room temperature for 16 hours under stirring.

After the completion of the reaction, the reaction product was poured into water, and after an addition of an aqueous sodium sulfite solution, extracted with ethyl acetate. The extract layer was washed with water, and dried over anhydrous sodium sulfate. Then, the solvent was distilled off under reduced pressure, and the residue was purified by silica gel column chromatography (developer: methylene chloride) to obtain 1.47 g of 3-(2,2,2-trifluoroethoxymethyl)-2-thiophenesulfonamide having a melting point of from 66° to 68° C.

Synthesis of intermediate, alternative method

[B-1] 40.3 g of chlorosulfonic acid was added to 100 ml of chloroform, and then 58.8 g of phosphorus pentachloride was gradually added thereto under stirring at −5° C. Thirty minutes later, 50 g of 3-bromomethylthiophene was dropwise added thereto at 0° C., and the mixture was stirred for 2 hours, then heated and reacted at a refluxing temperature for 1 hour.

After the completion of the reaction, the reaction product was poured into ice water, and the chloroform layer was separated. The chloroform layer was washed with water and dried over anhydrous sodium sulfate, and then chloroform was distilled off under reduced pressure. The residue thus obtained was washed with n-hexane and dried to obtain 71.8 g of 3-bromomethyl-thiophene-2-sulfonyl chloride having a melting point of from 40° to 46° C.

[B-2] In 160 ml of tetrahydrofuran, 40 g of the sulfonyl chloride obtained in the preceding step [B-1] was dissolved, and then ammonia gas was introduced and reacted under stirring at a temperature of from −15 to −10° C. until the heat generation ceased.

After the completion of the reaction, the reaction product was poured into water, and precipitated crystals were collected by filtration and dried to obtain 31.84 g of 3-bromomethylthiophene-2-sulfonamide having a melting point of from 153° to 157° C.

[B-3] 2 g of the sulfonamide obtained in the preceding step [B-2], 1.56 g of 2,2,2-trifluoroethanol and a 50% aqueous solution obtained by dissolving 1.56 g of sodium hydroxide in water were mixed, and 0.2 g of dodecyltrimethylammonium chloride was added thereto. The mixture was reacted at room temperature for 1 hour under stirring.

After the completion of the reaction, the reaction product was poured into water, adjusted to be weakly acidic with concentrated hydrochloric acid, and then extracted with ethyl acetate. The extract layer was washed with water and dried over anhydrous sodium sulfate, and then the solvent was distilled off under reduced pressure to obtain 1.46 g of 3-(2,2,2-trifluoroethoxymethyl)-2-thiophenesulfonamide having a melting point of from 52° to 56° C.

Synthesis of the desired product 0.12 g of 1,8-diazabicyclo[5.4.0]-7-undecene was added to a solution obtained by dissolving 0.21 g of 3-(2,2,2-trifluoroethoxymethyl)-2-thiophenesulfonamide obtained in the preceding step [A-4] and 0.21 g of phenyl N-(4,6-dimethoxypyrimidin-2-yl)carbamate in 5 ml of dried acetonitrile, and the mixture was reacted at room temperature for 17 hours under stirring.

After the completion of the reaction, water was added to the reaction product, and the mixture was acidified with dilute hydrochloric acid. Precipitated crystals were collected by filtration and dried to obtain 0.22 g of the desired product having a melting point of from 129° to 131° C.

SYNTHESIS EXAMPLE 2

Preparation of N-[(4,6-dimethoxypyrimidin-2-yl)aminocarbonyl]-3-(2-fluoroethoxymethyl)-2-thiophenesulfonamide (Compound No. 3)

Synthesis of intermediate

[1] 0.50 g of the sulfonamide obtained in the same manner as in the step [A-2] of Synthesis Example 1 and 0.123 g of 2-fluoroethanol were dissolved in 30 ml of dried ether, and 0.154 g of sodium hydride (purity: 60%) was added thereto. The mixture was reacted to a refluxing temperature for 3 hours.

After the completion of the reaction, the reaction product was cooled, and after an addition of water, adjusted to a pH of 3 or lower with dilute hydrochloric acid, and extracted with ethyl ether. The extract layer was dried over anhydrous sodium sulfate, and then the solvent was distilled off. The residue was purified by column chromatography (developer: methylene chloride/toluene=1/1) to obtain 0.355 g of N-tert-butyl-3-(2-fluoroethoxymethyl)-2-thiophenesulfonamide as an oily substance.

[2] 0.355 g of the sulfonamide obtained in the preceding step [1] and 5 ml of trifluoroacetic acid were mixed and reacted at room temperature for 16 hours under stirring.

After the completion of the reaction, the reaction product was poured into water, and after an addition of an aqueous sodium sulfite solution, extracted with ethyl acetate. The extract layer was washed with water and dried over anhydrous sodium sulfate, and then the solvent was distilled off under reduced pressure. The residue was purified by silica gel column chromatography (developer: methylene chloride/ethyl acetate=9/1) to obtain 0.222 g of 3-(2-fluoroethoxymethyl)-2-thiophenesulfonamide as an oily substance.

Synthesis of the desired product 0.141 g of 1,8-diazabicyclo[5.4.0]-7-undecene was added to a solution obtained by dissolving 0.222 g of 3-(2-fluoroethoxymethyl)-2-thiophenesulfonamide obtained in the preceding step [2] and 0.255 g of phenyl N-(4,6-dimethoxypyrimidin-2-yl)carbamate in 5 ml of dried acetonitrile, and the mixture was reacted at room temperature for 17 hours under stirring.

After the completion of the reaction, water was added to the reaction product, and the mixture was acidified with dilute hydrochloric acid. Precipitated crystals were collected by filtration and dried to obtain 0.334 g of the desired product having a melting point of from 121° to 123° C.

SYNTHESIS EXAMPLE 3

Preparation of N-[(4,6-dimethoxypyrimidin-2-yl)aminocarbonyl]-2-(2-fluoroethoxymethyl)-3-thiophenesulfonamide (Compound No. 9)

Synthesis of intermediate

[1] 25 g of 3-bromothiophene was dissolved in 200 ml of dried ethyl ether in a nitrogen stream, and the solution was cooled to −70° C. Then, 100 ml of a n-butyllithium solution (1.55 M) was dropwise added thereto at −50° C. or lower, and then the mixture was stirred at room temperature for 2 hours. This solution was again cooled to a temperature of −40° C. or lower, and sulfur dioxide gas was blown into the solution. Then, the temperature was gradually raised to room temperature, and the solvent was distilled off under reduced pressure. A white solid substance thus obtained was dissolved in a solution comprising 150 ml of water and 100 ml of isopropanol, and 22.5 g of N-chlorosuccinimide was added thereto at a temperature of 10° C. or lower. The mixture was reacted at room temperature for 1 hour. The reaction product was poured into water, and extracted with methylene chloride. The extract layer was washed with water and dried over anhydrous sodium sulfate, and then the solvent was distilled off. To the residue thus obtained, 150 ml of toluene was added, and 35.2 ml of tert-butylamine was further added at a temperature of 30° C. or lower. The mixture was reacted at a refluxing temperature for 15 hours.

After the completion of the reaction, the reaction product was cooled, then poured into water, acidified with hydrochloric acid and then extracted with ethyl acetate. The extract layer was washed with water and dried over anhydrous sodium sulfate, and then solvent was distilled off. The residue thus obtained was purified by silica gel column chromatography (developer: methylene chloride) to obtain 20.83 g of N-tert-butyl-3-thiophenesulfonamide having a melting point of from 90° to 92° C.

[2] In a nitrogen stream, 8.5 g of the thiophenesulfonamide obtained in the preceding step [1] was dissolved in a solvent mixture comprising 80 ml of dried ethyl ether and 20 ml of dried tetrahydrofuran, and the solution was cooled to −70° C. Then, 77 ml of a n-butyllithium solution (1.55 M) was dropwise added thereto at a temperature of −50° C. or lower. Then, the mixture was reacted at −70° C. for 1 hour. To this reaction product, 100 ml of dried tetrahydrofuran was added. Then, 3.5 g of paraformaldehyde was quickly added thereto at a temperature of −50° C. or lower, and the temperature was gradually raised to room temperature. Then, the mixture was reacted at room temperature for 3 hours.

After the completion of the reaction, the reaction product was poured into water, then acidified with dilute hydrochloric acid and extracted with ethyl acetate. The extract layer was washed with water and dried over anhydrous sodium sulfate, and then the solvent was distilled off under reduced pressure. The residue thus obtained was purified by silica gel column chromatography (developer: ethyl acetate/hexane=2/3) to obtain 2.98 g of N-tert-butyl-2-hydroxymethyl-3-thiophenesulfonamide as an oily substance.

[3] To 10 ml of thionyl chloride, 2.9 g of the thiophenesulfonamide obtained in the preceding step [2] was dropwise added, and the mixture was reacted at room temperature for 1 hour.

After the completion of the reaction, the reaction product was poured into ice water, and extracted with methylene chloride. The extract layer was washed with water, and dried over anhydrous sodium sulfate, and then the solvent as distilled off to obtain 2.6 g of N-tert-butyl-2-chloromethyl-3-thiophenesulfonamide as an oily substance.

[4] 2.6 g of the thiophenesulfonamide obtained in the preceding step [3] and 0.63 ml of 2-fluoroethanol were dissolved in 50 ml of dried ethyl ether, and 0.82 g of sodium hydride (60%) was gradually added at a temperature of 20° C. or lower. The mixture was reacted at room temperature for 5 hours.

After the completion of the reaction, the reaction product was poured into water, acidified with dilute hydrochloric acid, and extracted with methylene chloride. The extract layer was washed with water, and dried over anhydrous sodium sulfate, and then the solvent was distilled off. The residue thus obtained was purified by silica gel column chromatography (developer: methylene chloride) to obtain 2.2 g of N-tert-butyl-2-(2-fluoroethoxymethyl)-3-thiophenesulfonamide as an oily substance.

[5] 2.2 g of the thiophenesulfonamide obtained in the preceding step [4] was dissolved in 20 ml of trifluoroacetic acid, and reacted at 0° C. for 5 hours.

After the completion of the reaction, the reaction product was poured into water, neutralized with sodium hydrogen carbonate, and extracted with ethyl acetate. The extract layer was washed with water, and dried over anhydrous sodium sulfate, and then the solvent was distilled off under reduced pressure. The residue thus obtained was purified by silica gel column chromatography (developer: ethyl acetate/hexane=1/1) to obtain 1.21 g of 2-(2-fluoroethoxymethyl)-3-thiophenesulfonamide having a melting point of from 61° to 64° C.

Synthesis of the desired product 0.12 g of 2-(2-fluoroethoxymethyl)-3-thiophenesulfonamide obtained in the step [4] and 0.15 g of phenyl N-(4,6-dimethoxypyrimidin-2-yl)carbamate were dissolved in 5 ml of dried acetonitrile, and a solution obtained by dissolving 80 mg of 1,8-azabicyclo[5.4.0]-7-undecene in 1 ml of dried acetonitrile, was added thereto. The mixture was reacted at room temperature for 14 hours.

After the completion of the reaction, the reaction product was poured into water, and adjusted to a pH of from 3 to 5 with diluted hydrochloric acid. Precipitated crystals were collected by filtration, washed with water and dried under reduced pressure to obtain 0.15 g of the desired product having a melting point of from 141.5° to 144.5° C.

SYNTHESIS EXAMPLE 4

Preparation of
N-[(4,6-dimethoxypyrimidin-2-yl)aminocarbonyl]-4-(2-fluoroethoxymethyl)-3thiophenesulfonamide
(Compound No. 10)

Synthesis of intermediate

[1] In a nitrogen stream, 10.0 g of 3,4-dibromothiophene was dissolved in 100 ml of dried ethyl ether, and the solution was cooled to −70° C. Then, 26 ml of a n-butyllithium solution (1.55 M) was dropwise added thereto at −70° C., and then the mixture was stirred at this temperature for 2 hours. Sulfur dioxide gas was blown thereinto at a temperature of −40° C. or lower, and then the temperature was gradually raised to room temperature. The solvent was distilled off under reduced pressure, and the residue thus obtained was dissolved in a solution comprising 80 ml of water and 60 ml of isopropanol. Then, 6.1 g of N-chlorosuccinimide was added thereto at a temperature of 10° C. or lower. The mixture was reacted at a temperature of 10° C. or lower for 2 hours. The reaction product was poured into water, and extracted with methylene chloride. The extract layer was washed with water, and dried over anhydrous sodium sulfate, and then the solvent was distilled off. To the residue thus obtained, 50 ml of toluene was added, and 19 ml of tert-butylamine was further added thereto at a temperature of 30° C. or lower. The mixture was reacted at a refluxing temperature for 16 hours.

After the completion of the reaction, the reaction product was poured into ice water, acidified with dilute hydrochloric acid, and then extracted with methylene chloride. The extract layer was washed with water, and dried over anhydrous sodium sulfate, and then solvent was distilled off under reduced pressure. To the residue thus obtained, 40 ml of ethyl ether was added, and the residue was thoroughly pulverized. Crystals were collected by filtration, and washed with a solvent mixture (hexane/ethyl ether=1/1), and then dried to obtain 5.32 g of 4-bromo-N-tert-butyl-3-thiophenesulfonamide having a melting point of from 180° to 182° C.

[2] In a nitrogen stream, 2.0 g of the thiophenesulfonamide obtained in the preceding step [1] was dissolved in a solvent mixture comprising 20 ml of dried ethyl ether and 15 ml of dried tetrahydrofuran, and the solution was cooled to −70° C. Then, 9.5 ml of a n-butyllithium solution (1.55 M) was dropwise added at a temperature of −50° C. or lower, and the mixture was reacted at −70° C. for 1 hour. To the reaction product, 15 ml of dried tetrahydrofuran was added, and then 0.6 g of paraformaldehyde was quickly added at a temperature of −50° C. or lower. Then, the temperature was gradually raised to room temperature, and the mixture was reacted at room temperature for 1 hour.

After the completion of the reaction, the reaction product was poured into water, acidified with diluted hydrochloric acid, and extracted with ethyl acetate. The extract layer was washed with water, and dried over anhydrous sodium sulfate, and then the solvent was distilled off under reduced pressure. The residue thus obtained was purified by silica gel column chromatography (developer: ethyl acetate/hexane=1/1) to obtain 1.1 g of N-tert-butyl-4-hydroxymethyl-3-thiophenesulfonamide as an oily substance.

[3] To 7 ml of thionyl chloride, 1.1 g of the thiophenesulfonamide obtained in the preceding step [2] was dropwise added, and reacted at room temperature for 1.5 hours.

After the completion of the reaction, the reaction product was poured into ice water, and extracted with methylene chloride. The extract layer was washed with water, and dried over anhydrous sodium sulfate, and then the solvent was distilled off to obtain 1.0 g of N-tert-butyl-4-chloromethyl-3-thiophenesulfonamide as an oily substance.

[4] 1.0 g of the thiophenesulfonamide obtained in the preceding step [3] and 0.24 ml of 2-fluoroethanol were dissolved in 30 ml of dried ethyl ether, and 0.32 g of sodium hydride (60%) was gradually added at a temperature of 20° C. or lower. The mixture was stirred at room temperature for 3 hours, and further reacted at a refluxing temperature for 1 hour.

After the completion of the reaction, the reaction product was poured into water, acidified with dilute hydrochloric acid, and extracted with methylene chloride. The extract layer was washed with water, and dried over anhydrous sodium sulfate, and then the solvent was distilled off under reduced pressure. The residue thus obtained was purified by silica gel column chromatography (developer: methylene chloride) to obtain 0.7 g of N-tert-butyl-4-(2-fluoroethoxymethyl)-3-thiophenesulfonamide as an oily substance.

[5] 0.7 g of the thiophenesulfonamide obtained in the preceding step [4] was dissolved in 5 ml of trifluoroacetic acid, and reacted at 0° C. for 2 hours.

After the completion of the reaction, the reaction product was poured into water, neutralized with sodium hydrogen carbonate, and extracted with ethyl acetate. The extract layer was washed with water, and dried over anhydrous sodium sulfate, and then the solvent was distilled off under reduced pressure. The residue thus obtained was purified by silica gel column chromatography (developer: ethyl acetate/hexane=1/1) to obtain 0.4 g of 4-(2-fluoroethoxymethyl)-3-thiophenesulfonamide having a melting point of from 63.5° to 65.5° C.

Synthesis of the desired product 0.18 g of 4-(2-fluoroethoxymethyl)-3-thiophenesulfonamide obtained in the step [4] and 0.23 g of phenyl N-(4,6-dimethoxypyrimidin-2-yl)carbamate were dissolved in 8 ml of dried acetonitrile, and a solution obtained by dissolving 0.114 g of 1,8-diazabicyclo[5.4.0]-7-undecene in 5 ml of dried acetonitrile, was added thereto. The mixture was reacted at room temperature for 17 hours.

After the completion of the reaction, the reaction product was poured into water, and adjusted to a pH of from 3 to 5 with dilute hydrochloric acid. Precipitated crystals were collected by filtration, washed with water and then dried to obtain 0.29 g of the desired product having a melting point of from 153° to 155.5° C.

SYNTHESIS EXAMPLE 5

Preparation of N-[(4,6-dimethoxypyrimidin-2-yl)aminocarbonyl]-3-(2-chloroethoxymethyl)-2-thiophenesulfonamide (Compound No. 7)

Synthesis of intermediate

[1] 2.5 g of 3-bromomethyl-N-tert-butyl-2-thiophenesulfonamide obtained in the same manner as in the step [A-2] of Synthesis Example 1, and 0.92 g of ethyl glycolate, were dissolved in 50 ml of dried ethyl ether, and the solution was cooled. Then, 0.68 g of sodium hydride (60%) was gradually added thereto at a temperature of 20° C. or lower, and the mixture was reacted at room temperature for 15 hours.

After the completion of the reaction, the reaction product was poured into water, acidified with dilute hydrochloric acid, and extracted with methylene chloride. The extract layer was washed with water, and dried over anhydrous sodium sulfate, and then the solvent was distilled off under reduced pressure. The residue was purified by silica gel column chromatography (developer: hexane/methylene chloride=1/4) to obtain 1.43 g of ethyl 2-(tert-butylaminosulfonyl)-3-thenyloxyacetate as an oily substance.

[2] To 20 ml of dried ethyl ether, 0.18 g of lithium aluminum hydride was added, and cooled. Then, a solution obtained by dissolving 1.43 g of the oxyacetate obtained in the preceding step [1] in dried ether, was dropwise added thereto at a temperature of 20° C. or lower, and the mixture was reacted at room temperature for 14 hours.

After the completion of the reaction, the reaction product was poured into water, acidified with dilute hydrochloric acid, and extracted with ethyl acetate. The extract layer was washed with water, and dried over anhydrous sodium sulfate, and then the solvent was distilled off under reduced pressure to obtain 1.1 g of N-tert-butyl-3-(2-hydroxyethoxymethyl)-2-thiophenesulfonamide as an oily substance.

[3] 0.5 g of the thiophenesulfonamide obtained in the preceding step [2] was dissolved in 5 ml of dried pyridine, and the solution was cooled to a temperature of 0° C. or lower. Then, 0.27 g of phosphorus oxychloride was added thereto, and the mixture was reacted at 0° C. for 2 hours.

After the completion of the reaction, the solvent was distilled off under reduced pressure. Water was added to the residue, and the mixture was extracted with ethyl acetate. The extract layer was washed with water, and dried over anhydrous sodium sulfate, and then the solvent was distilled off under reduced pressure to obtain 0.33 g of N-tert-butyl-3-(2-chloroethoxymethyl)-2-thiophenesulfonamide as an oily substance.

[4] 0.33 g of the thiophenesulfonamide obtained in the preceding step [3] was dissolved in 5 ml of trifluoroacetic acid, and reacted at room temperature for 16 hours.

After the completion of the reaction, the reaction product was poured into water, neutralized with sodium hydrogen carbonate, and extracted with ethyl acetate. The extract layer was washed with water, and dried over anhydrous sodium sulfate, and then the solvent was distilled off under reduced pressure. The residue was purified by silica gel column chromatography (developer: methylene chloride) to obtain 0.12 g of 3-(2-chloroethoxymethyl)-2-thiophenesulfonamide as oily substance.

Synthesis of the desired product 0.12 g of the thiophenesulfonamide obtained in the preceding step [4] and 0.14 g of phenyl N-(4,6-dimethoxypyrimidin-2-yl)carbamate were dissolved in 5 ml of dried acetonitrile, and 1 ml of a dried acetonitrile solution containing 0.07 g of 1,8-diazabicyclo[5.4.0]-7-undecene was added thereto. The mixture was reacted at room temperature for 24 hours.

After the completion of the reaction, the reaction product was poured into water, and adjusted to a pH of from 3 to 5 with dilute hydrochloric acid. Precipitated crystals were collected by filtration, washed with water and dried to obtain 0.18 g of the desired product having a melting point of from 127° to 129° C.

SYNTHESIS EXAMPLE 6

Preparation of Compound No. 1

Synthesis of intermediate

[1] 603 mg of 3-(2,2,2-trifluoroethoxymethyl)-2-thiophenesulfonamide obtained in the same manner as in the step [A-4] of Synthesis Example 1, 238 mg of n-butyl isocyanate and 332 mg of potassium carbonate, were dissolved in 50 ml of dried acetone, and 10 mg of 1,4-diazabicyclo[2.2.2]octane was added thereto. The mixture was reacted at a refluxing temperature for 4 hours.

After the completion of the reaction, the reaction product was cooled, and the solvent was distilled off. Water was added to the residue. The mixture was adjusted to a pH of from 2 to 3 with dilute hydrochloric acid, and extracted with methylene chloride. The extracted layer was washed with a saturated sodium chloride aqueous solution, and dried over anhydrous sodium sulfate. Then, the solvent was distilled off. The residue was purified by silica gel column chromatography (developer: methylene chloride/ethyl acetate=8/2), and the solid product thus obtained was washed with n-hexane to obtain 807 mg of N-(n-butylaminocarbonyl)-3-(2,2,2-trifluoroethoxymethyl)-2-thiophenesulfonamide having a melting point of from 119° to 121.5° C.

[2] 372 mg of the thiophenesulfonamide obtained in the preceding step [1] and three drops of n-butyl isocyanate were dissolved in 30 ml of dried xylene, and phosgen was supplied at a refluxing temperature. When the temperature in the flask reached 95° C., the supply of phosgen was stopped, and the reaction was continued at that temperature for 30 minutes.

After the completion of the reaction, the reaction product was cooled, and the solvent was distilled off under reduced pressure to obtain 3-(2,2,2-trifluoroethoxymethyl)-2-thiophenesulfonyl isocyanate as a yellow oily substance.

Synthesis of the desired product

To the total amount of the thiophenesulfonyl isocyanate obtained in the preceding step [2], 10 ml of dioxane, 10 mg of 1,4-diazabicyclo-[2.2.2]octane and 154 mg of 2-amino-4,6-dimethoxy-1,3-pyrimidine were added, and the mixture was reacted at room temperature for 24 hours.

After the completion of the reaction, the solvent was distilled off from the reaction product, and water was added to the residue. Then, the mixture was extracted with methylene chloride. The extract layer was washed with water, and dried over anhydrous sodium sulfate, and then the solvent was distilled off. The residue was purified by silica gel column chromatography (developer: methylene chloride/ethyl acetate=8/2) to obtain 200 mg of the desired product having a melting point of from 129° to 131° C.

SYNTHESIS EXAMPLE 7

Preparation of Compound No. 1

Synthesis of the desired product 0.30 g of 3-(2,2,2-trifluoroethoxymethyl)-2-thiophenesulfonamide obtained in the same manner as in the step [A-4] of Synthesis Example 1 and 0.2 g of 2-isocyanato-4,6-dimethoxypyrimidine were added to 2 ml of anhydrous acetonitrile, and then 20 mg of 1,4-diazabicyclo-[2.2.2]-octane was added thereto. The mixture was reacted for 3 hours under cooling with ice, and for 1 hour and half at room temperature.

After the completion of the reaction, the reaction product was poured into water. Precipitated crystals were collected by filtration, and further dehydrated in an azeotropic dehydration apparatus by using benzene. Crystals were collected by filtration from benzene, and dried under reduced pressure to obtain 0.21 g of the desired product.

SYNTHESIS EXAMPLE 8

Preparation of Compound No. 1

Synthesis of the desired product

[1] 6 g of 3-(2,2,2-trifluoroethoxymethyl)-2-thiophenesulfonamide obtained in the same manner as in the step [A-4] of Synthesis Example 1 and 4.8 g of 2-isocyanato-4,6-dichloropyrimidine were added to 50 ml of anhydrous acetonitrile, and the mixture was reacted at a refluxing temperature for 1 hour.

After the completion of the reaction, the reaction product was poured into water. Precipitated crystals were collected by filtration and dried to obtain N-[(4,6-dichloropyrimidin-2-yl)aminocarbonyl]-3-(2,2,2-trifluoroethoxy)methyl-2-thiophenesulfonamide.

[2] The desired product is obtainable by subjecting the total amount of the thiophenesulfonamide obtained in the preceding step [1] to usual methoxylation.

Specific compounds of the present invention are shown in Table 1.

TABLE 1

Formula I: thiophene ring with positions 1(S), 2, 3, 4, 5; substituent X; substituent Y

[Y: —SO$_2$NHCONH—(triazine/pyrimidine with Z$_1$, Z$_2$, A)]

| Compound No. | Substituted position | X | Substituted position | A | Z$_1$ | Z$_2$ | Melting point (°C.) |
|---|---|---|---|---|---|---|---|
| 1 | 3 | —CH$_2$OCH$_2$CF$_3$ | 2 | CH | OCH$_3$ | OCH$_3$ | 129–131 |
| 2 | 3 | —CH$_2$OCH$_2$CF$_3$ | 2 | CH | OCH$_3$ | CH$_3$ | 114.5–117 |
| 3 | 3 | —CH$_2$OCH$_2$CH$_2$F | 2 | CH | OCH$_3$ | OCH$_3$ | 121–123 |
| 4 | 3 | —CH$_2$OCH$_2$CH$_2$F | 2 | CH | OCH$_3$ | CH$_3$ | 111–113 |
| 5 | 3 | —CH$_2$OCH$_2$CH$_2$F | 2 | CH | CH$_3$ | CH$_3$ | 128–132 |
| 6 | 3 | —CH$_2$OCH$_2$CH$_2$F | 2 | N | OCH$_3$ | OCH$_3$ | 104–108 |
| 7 | 3 | —CH$_2$OCH$_2$CH$_2$Cl | 2 | CH | OCH$_3$ | OCH$_3$ | 127–129 |
| 8 | 3 | —CH$_2$OCH$_2$CHF$_2$ | 2 | CH | OCH$_3$ | OCH$_3$ | 107–110 |
| 9 | 2 | —CH$_2$OCH$_2$CH$_2$F | 3 | CH | OCH$_3$ | OCH$_3$ | 141.5–144.5 |
| 10 | 4 | —CH$_2$OCH$_2$CH$_2$F | 3 | CH | OCH$_3$ | OCH$_3$ | 153–155.5 |
| 11 | 4 | —CH$_2$OCH$_2$CH$_2$F | 3 | CH | OCH$_3$ | CH$_3$ | 139–141 |
| 12 | 3 | —CH$_2$OCH$_2$CH$_2$CH$_2$F | 2 | CH | OCH$_3$ | OCH$_3$ | 118–121 |
| 13 | 3 | —CH$_2$OCF$_2$CF$_2$H | 2 | CH | OCH$_3$ | OCH$_3$ | 145–149 |
| 14 | 3 | —CH$_2$OCF$_2$CF$_2$H | 2 | N | OCH$_3$ | OCH$_3$ | 124–127 |
| 15 | 2 | —CH$_2$OCF$_2$CF$_2$H | 3 | CH | OCH$_3$ | OCH$_3$ | 159–160.5 |
| 16 | 3 | —CH$_2$OCH$_2$CF$_3$ | 2 | N | OCH$_3$ | OCH$_3$ | 139.5–142 |
| 17 | 3 | —CH$_2$OCH$_2$CF$_3$ | 2 | CH | CH$_3$ | CH$_3$ | 137–140 |
| 18 | 3 | —CH$_2$OCH(CH$_2$F)(CH$_2$F) | 2 | CH | OCH$_3$ | OCH$_3$ | 129.5–131 |
| 19 | 2 | —CH$_2$OCH$_2$CH$_2$F | 3 | CH | OCH$_3$ | CH$_3$ | 138–140 |
| 20 | 2 | —CH$_2$OCH$_2$CF$_3$ | 3 | CH | OCH$_3$ | OCH$_3$ | 137–141 |
| 21 | 2 | —CH$_2$OCH$_2$CHF$_2$ | 3 | CH | OCH$_3$ | OCH$_3$ | 119.5–122 |
| 22 | 3 | —CH$_2$OC(CH$_3$)(CF$_3$)(CH$_3$) | 2 | CH | OCH$_3$ | OCH$_3$ | 133–136 |
| 23 | 3 | —CH$_2$CH$_2$OCH$_2$CH$_2$CH$_2$Cl | 2 | CH | OCH$_3$ | OCH$_3$ | 114–116 |

Specific intermediates of the formula II-1 as the starting materials for the production of the compounds of the present invention, are given in Table 2.

TABLE 2

Formula II-1: thiophene ring with positions 1(S), 2, 3, 4, 5; substituent X$_3$ at position 3; —SO$_2$NH$_2$ at position 2

| Intermediate No. | Substituted position | X | Substituted position of SO$_2$NH$_2$ | Physical properties |
|---|---|---|---|---|
| 1 | 3 | —CH$_2$OCH$_2$CF$_3$ | 2 | Melting point 66–68° C. |
| 2 | 3 | —CH$_2$OCH$_2$CHF$_2$ | 2 | Brown oily substance |
| 3 | 3 | —CH$_2$OCH$_2$CH$_2$F | 2 | Colorless oily substance |
| 4 | 3 | —CH$_2$OCH$_2$CH$_2$Cl | 2 | Oily substance |
| 5 | 2 | —CH$_2$OCH$_2$CH$_2$F | 3 | Oily substance |
| 6 | 4 | —CH$_2$OCH$_2$CH$_2$F | 3 | Melting point 63.5–65.5° C. |
| 7 | 3 | —CH$_2$OCH$_2$CH$_2$CH$_2$F | 2 | Brown oily substance |
| 8 | 3 | —CH$_2$OCF$_2$CF$_2$H | 2 | Melting point 75–77° C. |
| 9 | 2 | —CH$_2$OCF$_2$CF$_2$H | 3 | White solid |

TABLE 2-continued

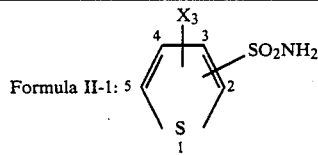

Formula II-1:

| Intermediate No. | X Substituted position | X | Substituted position of SO$_2$NH$_2$ | Physical properties |
|---|---|---|---|---|
| 10 | 3 | —CH$_2$OCH(CH$_2$F)(CH$_2$F) | 2 | Melting point 84–85.5° C. |
| 11 | 2 | —CH$_2$OCH$_2$CF$_3$ | 3 | Melting point 59–63° C. |
| 12 | 2 | —CH$_2$OCH$_2$CHF$_2$ | 3 | Colorless oily substance |
| 13 | 3 | —CH$_2$OC(CH$_3$)(CF$_3$)(CH$_3$) | 2 | Melting point 79–88° C. |
| 14 | 3 | —CH$_2$CH$_2$OCH$_2$CH$_2$CH$_2$Cl | 2 | Brown oily substance |

As will be evident from the Test Examples given hereinafter, the thiophenesulfonamide compounds of the present invention exhibit excellent herbicidal effects when used as active ingredients in herbicidal compositions. Particularly, they are capable of controlling, selectively and at a low dose, noxious weeds grown in paddy rice fields such as *Alisma canaliculatum, Cyperus difformis, Cyperus serotinus, Eleocharis acicularis, Eleocharis kuroguwai, Lindernia pyxidaria, Monochoria vaginalis, Rotala indica, Sagittaria pygmaea, Sagittaria trifolia* and *Scirpus juncoides,* without bringing about phytotoxicity against rice plants. Furthermore, they are capable of controlling such noxious weeds even when the weeds are in a relatively advanced stage of growth. Therefore, they are particularly effective for use as herbicides for paddy rice fields, although they are also useful for controlling noxious weeds in upland fields.

The herbicidal compositions of the present invention may be applied to various places such as orchards, vegetable gardens, forests, open grounds, factory sites, etc. in addition to the above-mentioned agricultural fields. Further, the manner of application may suitably be selected from the soil treatments and foliage treatments. For the application of the herbicidal compositions of the present invention, the active ingredients are usually mixed with various agricultural adjuvants such as a carrier, a diluent, a solvent, an emulsifier, an extender and a surfactant, as the case requires, and may be formulated in various formulations such as granules, dusts, wettable powders, emulsifiable concentrates or solutions. The weight ratio of the active ingredient to the agricultural adjuvants is usually from 0.01:99.99 to 90:10, preferably from 0.1:99.9 to 60:40. The suitable dose of the active ingredient can not simply be determined since it may vary depending upon the weather condition, the soil condition, the type of the formulation, the types of the weeds to be controlled, the season for the application, etc. However, it is usual that the effective dose is within a range of from 0.01 to 50 g/a, preferably from 0.1 to 50 g/a.

The herbicidal compositions of the present invention may be used in combination with or together with other agricultural chemicals, fertilizers, soils or phytotoxicity-reducing agents. In such a combination, they may exhibit even better effects or activities. In a case when they are used in combination with or together with other herbicides, the following compounds may be mentioned, for example, as the active ingredients of such other herbicides:

2,4-dichlorophenyl-3'-methoxy-4'-nitrophenyl ether, 2,4-dichlorophenyl-3'-methoxycarbonyl-4'-nitrophenyl ether, 2-chloro-2',6'-diethyl-N-(butoxymethyl)acetanilide, 2-chloro-2',6'-diethyl-N-(propoxyethyl)acetanilide, S-(2-methyl-1-piperidyl-carbonylmethyl)-O,O-di-n-propyldithiophosphate, S-(4-chlorobenzyl)N,N-diethylthio carbamate, S-benzyl-N-ethyl-N-(1,2-dimethylpropyl)thiol carbamate, S-ethyl-hexahydro-1H-azepin-1-carbothioate, S-(1-methyl-1-phenethyl) piperidine-1-carbothioate, 5-tert-butyl-3-(2,4-dichloro-5-isopropoxyphenyl)-1,3,4-oxadiazolin-2-one, benzthiazol-2-yloxy-acetic acid N-methylanilide, 4-(2,4-dichlorobenzoyl)-1,3-dimethyl-5-phenacyloxypyrazole, 4-(2,4-dichlorobenzoyl)-1,3-dimethylpyrazol-5-yl-p-toluene sulfonate, 4-(2,4-dichloro-3-methylbenzoyl)-1,3-dimethyl-5-phenacyloxypyrazole, 3,7-dichloro-8-quniolinecarboxylic acid, and S-benzyl-N-ethyl(1,2-dimethylpropyl)thiocarbamate.

Now, Test Examples of the herbicidal compositions of the present invention will be described.

TEST EXAMPLE 1

A pot of 1/5,000 are (are=100 m$^2$) was filled with paddy field soil, and seeds of *Scirpus juncoides* and tubers of *Sagittaria pygmaea* were sown. Then, the pot was kept in a wet condition. When *Scirpus juncoides* grew to a 1-leaf stage, water was poured in the pot to a depth of about 5 cm, and the wettable powder of the compound of the present invention was diluted with water and dropwise added to the pot by a pipette so that the amount of the active ingredient would be 2.5 g/are. Twenty days after the treatment, the growth of the weeds were visually observed, and the degree of growth inhibition was evaluated in accordance with the following standards (five grade ratings of from 1 to 5). The results are shown in Table 3.

Degree of growth inhibition

5: Withered completely
1: Grown in the same degree as the weeds in a non-treated region.

TABLE 3

| Compound No. | Degree of growth inhibition | | Compound No. | Degree of growth inhibition | |
|---|---|---|---|---|---|
| | Scirpus juncoides | Sagittaria pygmaea | | Scirpus juncoides | Sagittaria pygmea |
| 1 | 5 | 5 | 12 | 5 | 5 |
| 2 | 5 | 5 | 13 | 5 | 5 |
| 3 | 5 | 5 | 14 | 5 | 5 |
| 4 | 5 | 5 | 15 | 5 | 5 |
| 5 | 5 | 5 | 16 | 5 | 5 |
| 6 | 5 | 5 | 17 | 5 | 5 |
| 7 | 5 | 5 | 18 | 5 | 5 |
| 8 | 5 | 5 | 19 | 5 | 5 |
| 9 | 5 | 5 | 20 | 5 | 5 |
| 10 | 5 | 5 | 21 | 5 | 5 |
| 11 | 5 | 5 | 22 | 5 | 5 |

TEST EXAMPLE 2

A pot of 1/5,000 are was filled with paddy field soil, and seeds of *Scirpus juncoides* and tubers of *Sagittaria pygmaea* and *Cyperus serotinus* were sown. Then, the pot was kept in a wet condition. When *Scirpus juncoides* grew to a 1-leaf stage, water was poured into the pot to a depth of about 5 cm, and the wettable powder of the compound of the present invention was diluted with water, and dropwise added by a pipette so that the amount of the active ingredient would be as shown in Table 4. Twenty days after the treatment, the growth of the weeds was visually observed, and the degree of growth inhibition was evaluated in accordance with the same standards as specified in Test Example 1. The results are shown in Table 4.

Separately from the above test, a pot of 1/5,000 are was filled with paddy field soil. Water was introduced to the pot and the simulated paddy rice field was raked. One day later, rice plants of 2.5-leaf stage (species: Nihonbare) were transplanted (two seadlings per pot). Four days after the transplantation, the wettable powder of the compound of the present invention was diluted with water, and dropwise added by a pipette so that the amount of the active ingredient would be as shown in Table 4. Eight days after the treatment, the growth of the rice plants was visually observed, and evaluated in accordance with the same standards as in Test Example 1. The results are shown in Table 4.

TABLE 4

| Compound No. | Amount of the active ingredient (g/a) | Degree of growth inhibition | | | |
|---|---|---|---|---|---|
| | | Scirpus juncoides | Sagittaria pygmaea | Cyperus serotinus | Rice plant |
| 1 | 2.5/4 | 5 | 5 | 5 | 1 |
| 2 | 2.5/4 | 5 | 5 | 4 | 1 |
| 3 | 2.5/32 | 5 | 5 | 4 | 1 |
| 4 | 2.5/16 | 5 | 5 | — | 1 |
| 5 | 2.5/32 | — | 5–4 | — | 1 |
| 6 | 2.5/8 | 5 | 5 | — | 1 |
| 7 | 2.5/4 | 5 | 5 | 5 | 1 |
| 8 | 2.5/16 | 5 | 5 | 4 | 1 |
| 9 | 2.5/1 | 5 | 5 | 5 | 1 |
| 10 | 2.5/8 | 5 | 5 | 5 | 1 |
| 11 | 2.5/16 | 5 | 5 | — | 1 |
| 12 | 2.5/8 | 5 | 5 | 4 | 1 |
| 13 | 2.5/2 | 5 | 5 | — | 1 |
| 14 | 2.5/4 | 5 | 5–4 | — | 1 |
| 15 | 2.5/1 | 5 | 5 | — | 1 |
| 16 | 2.5/2 | 5 | 5–4 | — | 1 |
| 17 | 2.5/4 | — | 4–5 | — | 1 |
| 18 | 2.5/1 | 5 | 5 | — | 1 |
| 19 | 2.5/32 | 5 | 5 | — | 2 |
| 20 | 2.5 | 5–4 | 5 | 5 | 1 |
| 21 | 2.5/4 | 5 | 5–4 | — | 2 |
| 22 | 2.5/2 | 5 | 5–4 | — | 1 |

TEST EXAMPLE 3

A Wagner pot of 1/5,000 are is filled with paddy field soil. Then, seeds of *Panicum crus-galli* (barnyardgrass), *Scirpus juncoides* and *Monochoria vaginalis* are sown, tubers of *Sagittaria pygmaea* and *Cyperus serotinus* are planted, and rice seedlings of 2-leaf stage (species: Nihonbare) are transplanted (two seedlings per pot). When barnyardgrass grows to a 1.5-leaf stage, the wettable powder of each herbicide is diluted with water, and dropwise added by a pipette so that the amount of the active ingredient would be as shown in Table 5. Twenty-one days after the treatment, the growth is visually observed, and the degree of growth inhibition is evaluated in accordance with the following standards. The results are shown in Table 5.

| Standards for the degree of growth inhibition |
|---|
| 10: complete inhibition |
| 9: degree of remaining plant 1–10% |
| 8: degree of remaining plant 11–20% |
| 7: degree of remaining plant 21–30% |
| 6: degree of remaining plant 31–40% |
| 5: degree of remaining plant 41–50% |
| 4: degree of remaining plant 51–60% |
| 3: degree of remaining plant 61–70% |
| 2: degree of remaining plant 71–80% |
| 1: degree of remaining plant 81–100% |

TABLE 5

| Compound No. | Amount of the active ingredient (g/a) | Degree of growth inhibition | | | | | |
|---|---|---|---|---|---|---|---|
| | | Panicum crus-gali | Scirpus juncoides | Monochoria vaginalis | Sagittaria pygmaea | Cyperus serotinus | Rice plant |
| Compound No. 1 | 0.3 | 2 | 10 | 10 | 10 | 8 | 1 |
| Compound No. 8 | 0.15 | 5 | 10 | 10 | 10 | 7 | 1 |
| Compound No. 3 | 0.075 | 3 | 10 | 10 | 10 | 10 | 1 |
| Compound No. 9 | 0.075 | 3 | 10 | 10 | 10 | 8 | 1 |
| Compound No. 10 | 0.15 | 3 | 9 | 10 | 10 | 9 | 1 |
| Compound A | 2 | 10 | 1 | 4 | 1 | 1 | 1 |

TABLE 5-continued

| Compound No. | Amount of the active ingredient (g/a) | Degree of growth inhibition | | | | | |
|---|---|---|---|---|---|---|---|
| | | Panicum crusgali | Scirpus juncoides | Monochoria vaginalis | Sagittaria pygmaea | Cyperus serotinus | Rice plant |
| Compound B | 10 | 9 | 7 | 8 | 2 | 5 | 1 |
| Compound C | 15 | 8 | 5 | 7 | 1 | 3 | 1 |
| Compound D | 20 | 8 | 5 | 5 | 1 | 2 | 1 |
| Compound E | 4 | 10 | 7 | 5 | 3 | 5 | 1 |
| Compound F | 20 | 9 | 7 | 5 | 10 | 6 | 1 |
| Compound No. 1 + | 0.3 | 10 | 10 | 10 | 10 | 8 | 1 |
| Compound A | 2 | | | | | | |
| Compound No. 1 + | 0.3 | 10 | 10 | 10 | 10 | 10 | 1 |
| Compound B | 10 | | | | | | |
| Compound No. 1 + | 0.3 | 10 | 10 | 10 | 10 | 10 | 1 |
| Compound E | 4 | | | | | | |
| Compound No. 8 + | 0.15 | 10 | 10 | 10 | 10 | 8 | 1 |
| Compound A | 2 | | | | | | |
| Compound No. 3 + | 0.075 | 10 | 10 | 10 | 10 | 10 | 1 |
| Compound A | 2 | | | | | | |
| Compound No. 3 + | 0.075 | 10 | 10 | 10 | 10 | 10 | 1 |
| Compound B | 10 | | | | | | |
| Compound No. 3 + | 0.075 | 9 | 10 | 10 | 10 | 10 | 1 |
| Compound C | 15 | | | | | | |
| Compound No. 9 + | 0.075 | 10 | 10 | 10 | 10 | 9 | 1 |
| Compound A | 2 | | | | | | |
| Compound No. 9 + | 0.075 | 10 | 10 | 10 | 10 | 9 | 1 |
| Compound D | 20 | | | | | | |
| Compound No. 10 + | 0.15 | 10 | 10 | 10 | 10 | 10 | 1 |
| Compound E | 4 | | | | | | |
| Compound No. 10 + | 0.15 | 10 | 10 | 10 | 10 | 10 | 1 |
| Compound F | 20 | | | | | | |

Note:
Compound A: 3,7-Dichloro-8-quinolinecarboxylic acid
Compound B: S—(2-methyl-piperidyl-carbonylmethyl-O,O—di-n-propyldithio phosphate
Compound C: S—Benzyl-ethyl(1,2-dimethylpropyl)-thiocarbamate
Compound D: S—(1-methyl-1-phenethyl)-piperidine-1-carbothioate
Compound E: 2-Chloro-2',6'-diethyl-N—(propoxyethyl)-acetanilide
Compound F: 4-(2,4-dichlorobenzyl)-1,3-dimethyl-5-phenacyloxypyrazole Now, Formulation Examples of the herbicidal compositions of the present invention will be described.

FORMULATION EXAMPLE 1

| | |
|---|---|
| (1) Zeeklite | 78 parts by weight |
| (2) Lavelin S (tradename, manufactured by Daiichi Kogyo Seiyaku K.K.) | 2 parts by weight |
| (3) Sorpol 5039 (tradename, manufactured by Toho Kagaku Kogyo K.K.) | 5 parts by weight |
| (4) Carplex (tradename, manufactured by Shionogi & Co., Ltd.) | 15 parts by weight |

A mixture of the above components (1) to (4), and the Compound No. 1 of the present invention are mixed in a weight ratio of 9:1 to obtain a wettable powder.

FORMULATION EXAMPLE 2

| | |
|---|---|
| (1) Diatomaceous earth | 92.5 parts by weight |
| (2) Dikssol W-66 (tradename, manufactured by Daiichi Kogyo Seiyaku K.K.) | 5.0 parts by weight |
| (3) Dikssol W-09B (tradename, manufactured by Daiichi Kogyo Seiyaku K.K.) | 2.0 parts by weight |
| (4) Compound No. 3 of the present invention | 0.5 part by weight |

The above components are mixed to obtain a wettable powder.

FORMULATION EXAMPLE 3

| | |
|---|---|
| (1) Hi-Filler No. 10 (tradename, manufactured by Matsumura Sangyo K.K.) | 33 parts by weight |
| (2) Sorpol 5050 (tradename, manufactured by Toho Kagaku Kogyo K.K.) | 3 parts by weight |
| (3) Sorpol 5073 (tradename, manufactured by Toho Kagaku Kogyo K.K.) | 4 parts by weight |
| (4) Compound No. 8 of the present invention | 60 parts by weight |

The above component are mixed to obtain a wettable powder.

FORMULATION EXAMPLE 4

| | |
|---|---|
| (1) Newlite (tradename, manufactured by Nippon Taika Genryo K.K.) | 97 parts by weight |
| (2) Dikssol W-92 (tradename, manufactured by Daiichi Kogyo Seiyaku K.K.) | 2 parts by weight |
| (3) Compound No. 9 of the present invention | 1 part by weight |

The above components are mixed and pulverized to obtain a dust.

FORMULATION EXAMPLE 5

| (1) Water-soluble starch | 75 parts by weight |
|---|---|
| (2) Sodium lignin sulfonate | 5 parts by weight |
| (3) Sodium salt of Compound No. 10 of the present invention | 20 parts by weight |

The above components are mixed to obtain a water-soluble powder.

FORMULATION EXAMPLE 6

| (1) Zeeklite | 25 parts by weight |
|---|---|
| (2) Bentonite | 66.8 parts by weight |
| (3) Sorpol 5146 (tradename, manufactured by Toho Kagaku Kogyo K.K.) | 6 parts by weight |
| (4) Noigen FA-112 (tradename, manufactured by Daiichi Kogyo Seiyaku K.K.) | 2 parts by weight |
| | 2 parts by weight |
| (5) Compound No. 1 of the present invention | 0.2 part by weight |

The above components are mixed to obtain a granule.

We claim:

1. A thiophenesulfonamide compound having the formula:

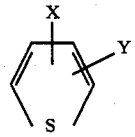 (I)

wherein X is a halogenalkoxyalkyl group having from 1 to 6 halogen atoms, the alkoxy moiety contains from 1 to 6 carbon atoms, and the alkyl group has 1 to 2 carbon atoms; Y is

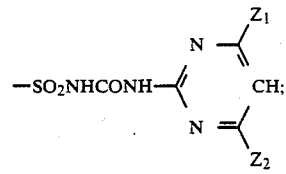

and each of $Z_1$ and $Z_2$ is a methyl group or a methoxy group; and its salt.

2. The compound according to claim 1, wherein each of $Z_1$ and $Z_2$ is a methoxy group.

3. The compound according to claim 1, wherein the halogenoalkoxyalkyl group as X contains an alkoxy moiety of from 1 to 3 carbon atoms, 1 to 4 halogen atoms, and an alkyl group having one carbon atom.

4. The compound according to claim 1, wherein the halogen in the halogenoalkoxyalkyl group is fluorine.

5. The compound according to claim 1, which is N-[(4,6-dimethoxypyrimidin-2-yl)aminocarbonyl]-2-(2-fluoroethoxymethyl)-3-thiophenesulfonamide.

6. The compound according to claim 1, which is N-[(4,6-dimethoxypyrimidin-2-yl)aminocarbonyl]-4-(2-fluoroethoxymethyl)-3-thiophenesulfonamide.

7. The compound according to claim 1, which is N-[(4,6-dimethoxypyrimidin-2-yl)aminocarbonyl]-3-(2-fluoroethoxymethyl)-2-thiophenesulfonamide.

8. The compound according to claim 1, which is N-[(4,6-dimethoxypyrimidin-2-yl)aminocarbonyl]-3-(2,2,2-trifluoroethoxymethyl)-2-thiophenesulfonamide.

9. The compound according to claim 1, which is N-[(4,6-dimethoxypyrimidin-2-yl)aminocarbonyl]-3-(2,2-difluoroethoxymethyl)-2-thiophenesulfonamide.

10. A herbicidal composition comprising a herbicidally effective amount of the thiophenesulfonamide compound of the formula I as defined in claim 1 or its salt, and an agricultural adjuvant.

11. The herbicidal composition according to claim 10, wherein the weight ratio of the thiophenesulfonamide compound or its salt to the agricultural adjuvant is from 0.01:99.99 to 90:10.

12. A method for killing weeds, which comprises applying a herbicidally effective amount of the thiophenesulfonamide compound of the formula I as defined in claim 1 or its salt to the locus to be protected.

13. The method according to claim 12, wherein the herbicidally effective amount is from 0.03 to 10 g/a.

* * * * *